United States Patent
Wang et al.

[11] Patent Number: 5,998,414
[45] Date of Patent: Dec. 7, 1999

[54] TROPONYL PIPERAZINES AS DOPAMINE D4 RECEPTOR LIGANDS

[75] Inventors: Xin Wang, Kirkland, Canada; Jian-min Fu, Elmsford, N.Y.; Adi M. Treasurywala, Mississauga, Canada

[73] Assignee: Hoechst Marion Roussel, Inc., Bridgewater, N.J.

[21] Appl. No.: 08/907,672

[22] Filed: Aug. 8, 1997

Related U.S. Application Data

[60] Provisional application No. 60/059,975, Aug. 22, 1996.

[51] Int. Cl.$^6$ .................. A61K 31/495; C07D 295/116; C07D 295/155; C07D 405/06
[52] U.S. Cl. ................. 514/253; 514/252; 514/255; 544/376; 544/377; 544/379; 544/399
[58] Field of Search .................... 544/399, 376, 544/377, 379; 514/255, 252, 253

[56] References Cited

U.S. PATENT DOCUMENTS

| | | | |
|---|---|---|---|
| 4,351,832 | 9/1982 | Rakhit et al. | 424/246 |
| 4,469,693 | 9/1984 | Bagli | 424/250 |
| 4,469,694 | 9/1984 | Bagli | 424/250 |
| 4,469,695 | 9/1984 | Bagli | 424/250 |
| 4,764,609 | 8/1988 | Weigel et al. | 544/250 |
| 5,541,179 | 7/1996 | Baudy | 514/212 |
| 5,563,150 | 10/1996 | Curtis | 514/300 |

FOREIGN PATENT DOCUMENTS

| | | |
|---|---|---|
| 0148612 | 7/1981 | European Pat. Off. . |
| 0034894 | 9/1981 | European Pat. Off. . |
| 8103022 | 10/1981 | WIPO . |
| 9204338 | 3/1992 | WIPO . |
| 9413649 | 6/1994 | WIPO . |

OTHER PUBLICATIONS

Miller, et al, *Advances in CNS Drug–Receptor Interactions*, vol. 1, 75–129, 1991.
Sehgal, S.N., *Jrnl of Industrial Microbiology*, vol. 29, 1988, pp. 231–235.
Hicks, D.R. et al, *Jrnl of Labeled Compounds and Radiopharmaceuticals*, vol. XXV, No. 12.
Seeman, Philip et al, *Advances in Experimental Medicine and Biology*, vol. 235, pp. 55–63.
Koller, William C. et al., *Clinical Neuropharmacology*, vol. 11, No.3, pp. 221–231, 1988.
Koller, William. C. et al., *Neuropharmacology*, vol. 25, No. 9, 1986, pp. 973–979.
Seeman, Philip et al., *Molecular Pharmacology*, 28:391–399.
Voith, Katherine, *Psychopharmacology* (1985) 85: 405–409.
Voith, Katherine, *Drug Development Research*, 4:391–404, (1984).
Ahmed, F.R. et al., *CAN J. Chem*, vol. 60, 1982, pp. 2687–2692.
Kocjan, Darko, *J. Med. Chem*, 1994, 37, pp. 2851–2855.
Bagli et al., *J. of Med. Chem*. 29, p. 186 (1986).
Bagli et al., *J of Med Chem*. 27 p. 875 (1984).
Vantol et al. *Nature*, vol. 350, p 610–614, 1991.
Waddington, *Gen. Pharmac.* vol. 19, p 55–60, 1988.

*Primary Examiner*—Emily Bernhardt
*Attorney, Agent, or Firm*—Carolyn D. Moon

[57] ABSTRACT

Described herein are compounds of the general formula:

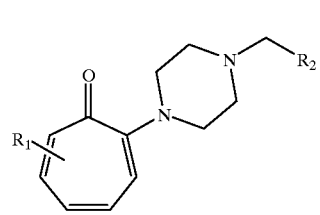

I a stereoisomer, solvate, or pharmaceutically acceptable salt thereof, wherein:

$R_1$ is H, halo, aryl or aryl substituted with one or two groups independently selected from halo, $C_{1-4}$alkyl, $C_{1-4}$-alkoxy, nitro, trifluoromethyl, trifluoromethoxy or cyano;

$R_2$ is $C_{4-9}$alkyl; phenyl or phenyl substituted with one or two groups selected independently from OH, cyano, halo, $C_{1-4}$alkoxy, $C_{1-4}$alkyl, trifluoromethyl, trifluoromethoxy, nitro or phenyl; naphthyl;

phenyl fused to a 5 or 6-membered heterocycle; the coumarin moiety

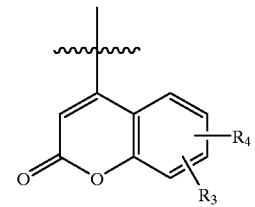

wherein $R_3$ and $R_4$ are selected independently from H, $C_{1-4}$alkyl and $C_{1-4}$alkoxy;
or 1,2-methylenedioxy phenyl;
with the proviso that $R_2$ is not phenyl or 3,4-dimethoxyphenyl when $R_1$ is H.

Also described is their use as pharmaceuticals to treat indications in which the D4 receptor is implicated, such as schizophrenia and anxiety.

23 Claims, No Drawings

TROPONYL PIPERAZINES AS DOPAMINE D4 RECEPTOR LIGANDS

This application claims the benefit of U.S. Provisional Application Ser. No. 60/059,975 filed Aug. 22, 1996.

This invention relates to compounds that bind to the dopamine D4 receptor, to their preparation and their use for therapeutic and drug screening purposes.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some drugs currently on the market in fact exhibit the desired antagonism of D4 receptor activity, and bind with relative strong affinity to the receptor. Yet because of their structure, these drugs interact also with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the dibenzodiazepine, clozapine, and the dibenzoxazepine, isoloxapine. Analysis of their dopamine receptor binding properties has shown that the preference for binding the D4 receptor relative to the D2 receptor is about 10 fold, for both products. Similarly, both bind the D4 receptor with about the same affinity (Ki value approximately 20 nM). Other products, recently published in the scientific literature, have shown similar D4 to D2 selectivity profile and D4 affinity values.

The use of certain troponyl piperazines as dopamine receptor agonists, for example to treat Parkinsonism and other related disorders, is described in EP 034,894 and in related scientific articles (see Bagli, J. et al., J. Med. Chem. 1984, 27:875 and Bagli, J. et al., J. Med. Chem. 1986, 29:186).

It is an object of the present invention to provide a compound that binds to the D4 receptor.

It is an object of the present invention to provide D4 receptor-binding compounds.

It is another object of the present invention to provide compounds which bind selectively to the D4 receptor, relative particularly to the D2 receptor.

It is a further object of the present invention to provide a pharmaceutical composition comprising a compound of the present invention, as active ingredient.

It is another object of the present invention to provide a method effective to treat medical conditions for which administration of a D4 receptor antagonist is indicated, such as to treat schizophrenia and anxiety.

SUMMARY OF THE INVENTION

According to one aspect of the present invention, there is provided a compound of Formula I:

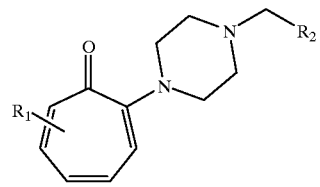

I a stereoisomer, solvate, or pharmaceutically acceptable salt thereof,
wherein:
$R_1$ is H, halo, aryl or aryl substituted with one or two groups independently selected from halo, $C_{1-4}$alkyl, $C_{1-4}$alkoxy, nitro, trifluoromethyl, trifluoromethoxy or cyano;

$R_2$ is $C_{4-9}$alkyl; phenyl or phenyl substituted with one or two groups selected independently from OH, cyano, halo, $C_{1-4}$alkoxy, $C_{1-4}$alkyl, trifluoromethyl, trifluoromethoxy, nitro or phenyl; naphthyl; phenyl fused to a 5 or 6-membered heterocycle; the coumarin moiety

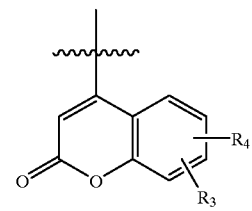

wherein $R_3$ and $R_4$ are selected independently from H, $C_{1-4}$alkyl and $C_{1-4}$alkoxy;

or 1,2-methylenedioxy phenyl;
with the proviso that $R_2$ is not phenyl or 3,4-dimethoxyphenyl when $R_1$ is H.

According to another aspect of the invention, there is provided a pharmaceutical composition comprising a compound of Formula I and II in an amount effective to antagonize D4 receptor stimulation and a pharmaceutically acceptable carrier;

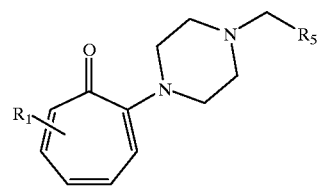

II wherein:
$R_1$ is selected independently from H, halo, aryl and aryl substituted with one or two groups independently selected from H, halo, $C_{1-4}$alkyl, $C_{1-4}$alkoxy, nitro, trifluoromethyl, trifluoromethoxy and cyano.

$R_5$ is selected independently from $C_{4-9}$alkyl; phenyl or phenyl substituted with one or two groups selected independently from OH, cyano, halo, $C_{1-4}$alkoxy, $C_{1-4}$alkyl, trifluoromethyl, trifluoromethoxy, nitro or phenyl; naphthyl; phenyl fused to a 5 or 6-membered heterocycle; the coumarin moiety

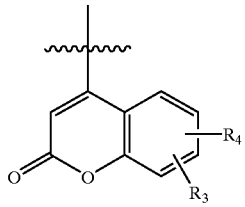

wherein $R_3$ and $R_4$ are selected independently from H, $C_{1-4}$alkyl and $C_{1-4}$alkoxy;

or 1,2-methylenedioxy phenyl.

This is essentially Formula I without the provisio. Formula II is to be used as a pharmaceutical composition.

In another of its aspects, the invention provides the use of compounds of Formulas I and II as D4 receptor antagonists for the treatment of medical conditions mediated by inhibition of D4 receptor antagonism, and use in treating schizophrenia and anxiety.

In a further aspect of the invention, there is provided an analytical method in which a compound of the invention is used to distinguish, in a receptor population, the D4 receptor from other receptor types, and particularly from the D2 receptor. These and other aspects of the present invention are now described in greater detail hereinbelow.

DETAILED DESCRIPTION AND PREFERRED EMBODIMENTS

Definitions

The term "$C_{4-9}$alkyl" as used herein means straight alkyl radicals containing from four to nine carbon atoms and branched chain alkyl radicals containing six to eight carbon atoms and includes pentyl, hexyl, 1-methylhexyl and the like.

The term "$C_{1-4}$alkyl" as used herein means straight alkyl radicals containing from one to four carbon atoms and branched chain alkyl radicals containing three or four carbon atoms and includes methyl, ethyl, propyl, 1-methylethyl, butyl, 1-methylpropyl and the like. 1-Methylethyl and 1-methylpropyl are also known as isopropyl and sec-butyl respectively.

The term "$C_{1-4}$alkoxy" as used herein means straight chain alkoxy radicals containing from one to four carbon atoms and branched chain alkoxy radicals containing three to four carbon atoms and includes methoxy, ethoxy, 1-methylethoxy, propyloxy, butoxy and the like.

The term "halo" as used herein means halide and includes fluoro, chloro, bromo and iodo.

The term "heterocycle" as used herein means a five or six membered saturated or unsaturated ring wherein the heterocycle contains one to three heteroatoms independently selected from nitrogen, oxygen and sulfur and includes 1,3-dioxole, thiophene, furan, pyrrole, imidazole, pyrazole, pyrrolidine, pyrroline, imidazolidine, pyrazolidine, pyrazoline, pyran, pyridine, pyrazine, pyrimidine, pyridazine, piperidine, piperazine, morpholine, and the like. Thus, some examples of "phenyl fused to a 5 or 6 membered heterocycle" are benzothiophene, isobenzofuran, chromene, indole, isoindole, indazole, isoquinoline, quinoline, phtalazine, quinoxaline, quinazoline, cinnoline, isochroman, chroman, indoline, isoindoline, and the like.

The term aryl as used herein means a five or six membered carbocyclic unsaturated ring system which is either an aromatic (such as phenyl) or heteroaromatic ring which contains one or two nitrogen atoms, one or two oxygen atoms, one nitrogen and one oxygen atom, one nitrogen and one sulfur atom, or one sulfur atom, and includes, but is not limited to, thiophene, furan, pyrrole, pyran, pyridine, pyrazine, pyrimidine, pyridazine, isothiazole, isoxazole, pyrazoline, and pyrazine. These aryls may be substituted as is appropriate to their chemical structure with one or two groups independently selected from halo, $C_{1-4}$ alkyl, $C_{1-4}$ alkoxy, nitro, trifluoromethyl, trifluoromethoxy and cyano. Preferably aryl is phenyl substituted at the meta or para position thereof with one substituent.

The term "pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

"Solvate" means a compound of Formula I or the pharmaceutically acceptable salt of Formula I wherein molecules of a suitable solvent are incorporated in a crystal lattice. A suitable solvent is not substantially toxic at the dosage administered as the solvate to achieve the desired effect. Examples of suitable solvents are ethanol and the like.

The term "stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

The term "patient" means a warm blooded animal, such as for example rat, mice, dogs, cats, guinea pigs, and primates such as humans.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "schizophrenia" means schizophrenia, schizophreniform disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington D.C.

The invention relates to compounds that bind the dopamine D4 receptor in a selective manner, relative to the dopamine D2 receptor.

In embodiments of the invention, compounds of Formula I and II include those in which $R_1$ is H and $R_2$ is $C_{4-9}$alkyl.

In a specific embodiment of the invention, a compound of Formula I and II has $R_1$ equal to H and $R_2$ equal to n-pentyl.

In another embodiment of the invention, compounds of Formula I and II include those in which $R_1$ is H and $R_2$ is selected from naphthyl, phenyl, phenyl substituted with one or two groups selected from methyl, methoxy, nitro, bromo, chloro, fluoro, trifluoromethoxy, trifluoromethyl, phenyl and cyano and phenyl fused to a 5 or 6-membered heterocycle.

In a specific embodiment of the invention, compounds of Formula I and II include those in which $R_1$ is H and $R_2$ is the following:
4-methylphenyl;
4-trifluoromethoxyphenyl;
4-trifluoromethylphenyl;
4-nitrophenyl;
3-cyanophenyl;
3-trifluoromethyphenyl;
4-bromophenyl;
3,5-difluorophenyl;
2-cyanophenyl;
2-chlorophenyl;
2-nitrophenyl;
3-methylphenyl;
2-phenylphenyl;
3-bromophenyl;
3,5-bis(trifluoromethyl)phenyl;
3-nitrophenyl;
4-cyanophenyl;
3-methoxyphenyl,;
2-naphthyl;
1,2-methylenedioxyphenyl; (preferably, $R_2$ together with the methylene to which it is attached form piperonyl)
4-chlorophenyl; and
3-chlorophenyl.

In another embodiment of the invention, compounds of Formula I and II are those in which $R_1$ is H and $R_2$ is the coumarin moiety shown below, and $R_3$ and $R_4$ are selected from H and $C_{1-4}$alkoxy.

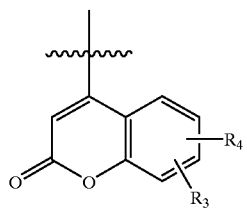

A specific embodiment of the invention includes compounds of Formula I and II where $R_1$ is H and $R_2$ is 1-(6,7-dimethoxycoumarin) and 1-(7-methoxycoumarin).

In another embodiment of the invention, compounds of Formula I and II include those in which $R_1$ is selected from halo, aryl and aryl substituted with one or two groups independently selected from H, halo, $C_{1-4}$alkyl, $C_{1-4}$alkoxy, nitro, trifluoromethyl, trifluoromethoxy and cyano and $R_2$ is selected from $C_{4-9}$alkyl, naphthyl, phenyl, phenyl substituted with one or two groups selected from methyl, methoxy, nitro, bromo, chloro, fluoro, trifluoromethoxy, trifluoromethyl, cyano and phenyl, phenyl fused to a 5 or 6-membered heterocycle and the coumarin moiety shown below, wherein $R_3$ and $R_4$ are selected from H and $C_{1-4}$alkoxy.

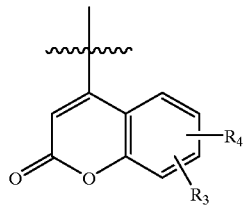

In more preferred embodiments of the invention, compounds Formula I and II include those in which $R^1$ is selected from halo and aryl attached at carbon 7 of the 7-membered ring and $R^2$ is phenyl substituted with one or two groups selected from methyl, methoxy, nitro, bromo, chloro, fluoro, trifluoromethoxy, trifluoromethyl, cyano and phenyl; or $R_2$ is naphthyl or a phenyl fused to a 5 or 6-membered heterocycle.

In specific embodiments of the invention, compounds Formula I and II include those in which $R^1$ is selected from bromo and thienyl attached at carbon 7 of the 7-membered ring and $R_2$ is selected from 1,2-methylenedioxyphenyl and phenyl substituted with chloro.

In specific embodiments of the invention, the compounds of Formula I and II include:

2-(4-benzyl-1-piperazinyl)-2,4,6-cycloheptatriene-1-one;
2-(4-piperonyl-1-piperazinyl)-2,4,6-cycloheptatriene-1-one;
2-(4-hexyl-1-piperazinyl)-2,4,6-cycloheptatriene-1-one,;
2-[4-(3-methoxybenzyl)-1-piperazinyl]-2,4,6-cycloheptatriene-1-one;
2-[4-(4-cyanobenzyl)-1-piperazinyl]-2,4,6-cycloheptatriene-1-one;
2-[4-(4-methylbenzyl)-1-piperazinyl]-2,4,6-cycloheptatriene-1-one;
2-[4-(4-trifluoromethoxybenzyl)-1-piperazinyl]-2,4,6-cycloheptatriene-1-one;
2-[4-(4-trifluoromethylbenzyl)-1-piperazinyl]-2,4,6-cycloheptatriene-1-one;
2-[4-(4-nitrobenzyl)-1-piperazinyl]-2,4,6-cycloheptatriene-1-one;

2-[4-(3-cyanobenzyl)-1-piperazinyl]-2,4,6-cycloheptatriene-1-one;
2-[4-(3-trifluoromethylbenzyl)-1-piperazinyl]-2,4,6-cycloheptatriene-1-one;
2-[4-(4-bromobenzyl)-1-piperazinyl]-2,4,6-cycloheptatriene-1-one;
2-(4-naphthyl-2-methyl)-1-piperazinyl]-2,4,6-cycloheptatriene-1-one;
2-[4-(3,5-difluorobenzyl)-1-piperazinyl]-2,4,6-cycloheptatriene-1-one;
2-[4-(2-chlorobenzyl)-1-piperazinyl]-2,4,6-cycloheptatriene-1-one;
2-[4-(3-methylbenzyl)-1-piperazinyl]-2,4,6-cycloheptatriene-1-one;
2-[4-(2-phenylbenzyl)-1-piperazinyl]-2,4,6-cycloheptatriene-1-one;
2-[4-(3-bromobenzyl)-1-piperazinyl]-2,4,6-cycloheptatriene-1-one;
2-{4-[3,5-bis(trifluoromethyl)benzyl]-1-piperazinyl}-2,4,6-cycloheptatriene-1-one;
2-[4-(3-nitrobenzyl)-1-piperazinyl]-2,4,6-cycloheptatriene-1-one;
2-[4-(3-chlorobenzyl)-1-piperazinyl]-2,4,6-cycloheptatriene-1-one;
2-[4-(4-chlorobenzyl)-1-piperazinyl]-2,4,6-cycloheptatriene-1-one;
7-bromo-2-[4-(4-chlorobenzyl)-1-piperazinyl]-2,4,6-cycloheptatriene-1-one;
7-bromo-2-(4-piperonyl-1-piperazinyl)-2,4,6-cycloheptatriene-1-one;
2-(4piperonyl-1-piperazinyl)-7-thien-2-yl-2,4,6-cycloheptatriene-1-one;
2-{4-[1-(6,7-dimethoxycoumarin)methyl]-1-piperazinyl}-2,4,6-cycloheptatriene-1-one; and
2-{4-[1-(7-methoxycoumarin)methyl]-1-piperazinyl}-2,4,6-cycloheptatriene-1-one.

Preferred for their enhanced D4 potency are the following Formula I and Formula II compounds:

2-(4-piperonyl-1-piperazinyl)-2,4,6-cycloheptatriene-1-one;
2-(4-hexyl-1-piperazinyl)-2,4,6-cycloheptatriene-1-one;
2-[4-(3-methoxybenzyl)-1-piperazinyl]-2,4,6-cycloheptatriene-1-one;
2-[4-(4-cyanobenzyl)-1-piperazinyl]-2,4,6-cycloheptatriene-1-one;
2-[4-(4-methylbenzyl)-1-piperazinyl]-2,4,6-cycloheptatriene-1-one;
2-[4-(4-trifluoromethoxybenzyl)-1-piperazinyl]-2,4,6-cycloheptatriene-1-one;
2-[4-(4-trifluoromethylbenzyl)-1-piperazinyl]-2,4,6-cycloheptatriene-1-one;
2-[4-(4-nitrobenzyl)-1-piperazinyl]-2,4,6-cycloheptatriene-1-one;
2-[4-(3-trifluoromethylbenzyl)-1-piperazinyl]-2,4,6-cycloheptatriene-1-one;
2-[4-(4-bromobenzyl)-1-piperazinyl]-2,4,6-cycloheptatriene-1-one;
2-(4-naphthyl-2-methyl)-1-piperazinyl]-2,4,6-cycloheptatriene-1-one;
2-[4-(3-bromobenzyl)-1-piperazinyl]-2,4,6-cycloheptatriene-1-one;
2-[4-(3-chlorobenzyl)-1-piperazinyl]-2,4,6-cycloheptatriene-1-one;
2-[4-(4-chlorobenzyl)-1-piperazinyl]-2,4,6-cycloheptatriene-1-one;
7-bromo-2-(4-piperonyl-1-piperazinyl)-2,4,6-cycloheptatriene-1-one; and
2-(4-piperonyl-1-piperazinyl)-7-thien-2-yl-2,4,6-cycloheptatriene-1-one;

Particularly preferred compounds of Formula I and Formula II include:

2-(4-piperonyl-1-piperazinyl)-2,4,6-cycloheptatriene-1-one;
2-[4-(3-methoxybenzyl)-1-piperazinyl]-2,4,6-cycloheptatriene-1-one;
2-[4-(4-cyanobenzyl)-1-piperazinyl]-2,4,6-cycloheptatriene-1-one;
2-[4-(4-bromobenzyl)-1-piperazinyl]-2,4,6-cycloheptatriene-1-one;
2-[4-(4-trifluoromethoxybenzyl)-1-piperazinyl]-2,4,6-cycloheptatriene-1-one;
2-[4-(4-trifluoromethylbenzyl)-1-piperazinyl]-2,4,6-cycloheptatriene-1-one;
2-[4-(4-nitrobenzyl)-1-piperazinyl]-2,4,6-cycloheptatriene-1-one;
2-[4-(3-chlorobenzyl)-1-piperazinyl]-2,4,6-cycloheptatriene-1-one;
2-[4-(4-chlorobenzyl)-1-piperazinyl]-2,4,6-cycloheptatriene-1-one;
2-[4-(4-methylbenzyl)-1-piperazinyl]-2,4,6-cycloheptatriene-1-one;
7-bromo-2-(4-piperonyl-1-piperazinyl)-2,4,6-cycloheptatriene-1-one; and
2-(4-naphthyl-2-methyl)-1-piperazinyl]-2,4,6-cycloheptatriene-1-one.

Most preferred compounds of Formula I and Formula II include:

2-(4-piperonyl-1-piperazinyl)-2,4,6-cycloheptatriene-1-one;
2-[4-(4-bromobenzyl)-1-piperazinyl]-2,4,6-cycloheptatriene-1-one;
2-[4-(4-trifluoromethylbenzyl)-1-piperazinyl]-2,4,6-cycloheptatriene-1-one;
2-[4-(4-trifluoromethoxybenzyl)-1-piperazinyl]-2,4,6-cycloheptatriene-1-one;
2-[4-(4-nitrobenzyl)-1-piperazinyl]-2,4,6-cycloheptatriene-1-one;
2-[4-(4-chlorobenzyl)-1-piperazinyl]-2,4,6-cycloheptatriene-1-one;
7-bromo-2-(4-piperonyl-1-piperazinyl)-2,4,6-cycloheptatriene-1-one; and
2-(4-naphthyl-2-methyl)-1-piperazinyl]-2,4,6-cycloheptatriene-1-one.

Acid addition salts of the compound of Formula I and II are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those known in the art. The present invention therefore provides, in a further aspect, a process for the preparation of a compound of Formula I and II wherein $R_1$ is H or halo or a salt, solvate or hydrate thereof, which comprises one of two possible processes. The first comprises coupling a reagent of Formula A:

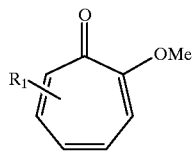

A with a reagent of Formula B:

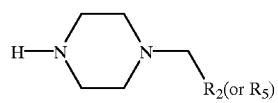

B in refluxing methanol as described in EP 034,894 and can be used when the corresponding reagent of Formula B is available by synthesis or commercial means.

Reagent (A), wherein $R_1$ is H or halo can be synthesized using established techniques where the appropriate tropolone is treated with a methylating reagent (see Pietra, F. Chem. Rev. 1973, 73:293 when $R^1$ is H and Takeshita, H.; Mori, A. Synthesis, 1986, 578 when $R^1$ is halo). For example, treating tropolone with dimethyl sulfate and potassium carbonate in acetone.

Compounds of Reagent B are either known, available commercially or can be prepared by conventional means. For example, a useful method for preparing a compound of Reagent B is described in EP 034,894.

A compound of Formula I and II may also be prepared by coupling a reagent of Formula C:

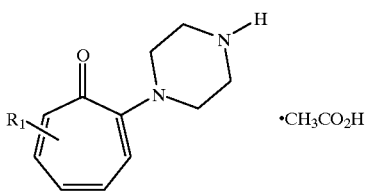

C with a reagent of Formula D:

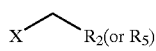

D

X = Cl, Br in the presence of base such as potassium carbonate in an enert organic solvent such as acetonitrile as described herein. Reagent C compounds, wherein $R_1$ is H or halo are synthesized using established techniques, for example by treating reagent A with piperazine according to the procedure described by Bagli (J. Med. Chem. 1984, 27:875). Reagent D can be obtained commercially or can be synthesized by established techniques, for example by treating the corresponding alcohol with halogenating reagents such as $CBr_4$ and triphenylphosphine (X=Br) or thionyl chloride (X=Cl).

Compounds of Formula I and II wherein $R_1$ is aryl or aryl substituted with one or two groups independently selected from H, halo, $C_{1-4}$alkyl, $C_{1-4}$alkoxy, nitro, trifluoromethyl, trifluoromethoxy and cyano can be prepared from compounds of Formula I and II wherein $R_1$ is halo using standard palladium catalysed cross coupling techniques in reactions with a metallo-aryl compound $R_1$—M, wherein $R_1$ is as defined above and M is an optionally substituted metal substituent, attached at any carbon node of the aryl group, suitable for cross-coupling reactions. Examples of such M groups include $(alkyl)_3Sn$—, $(alkyl)_2B$—, $(HO)_2B$—, $(alkoxy)_2B$—, Li, Cu, chloroZn or haloMg. The most preferred M group is chloroZn. The reaction takes place in an inert solvent, and optionally in the presence of base, lithium chloride and a suitable catalyst. Suitable catalysts included palladium (II) and palladium (0) species such as palladium (II) acetate, palladium (II) chloride and tetrakis(triphenylphosphine) palladium (0). The preferred catalyst is tetrakis(triphenylphosphine) palladium (0). Suitable inert solvents include acetonitrile, N,N-dimethylformamide and tetrahydrofuran, with tetrahydrofuran being preferred. The reaction takes place at a temperature of from 25–100° C., preferably 50–100° C. Compounds of formula $R_1$—M can be prepared from reagents of $R_1$—Y, wherein Y is halo or triflate, by standard metallation reactions either independently or in situ. For example, the compound $R_1$—M wherein M is chloro-Zn can be prepared, in an in situ fashion prior to the cross coupling reaction, by treating $R_1$—Br with n-butyl lithium and zinc chloride In tetrahydrofuran at −78° C.

The clozapine-like binding profile of the present compounds indicates their utility as pharmaceuticals that may be useful as a neuroleptic for the treatment of various conditions in which D4 receptor stimulation is implicated, such as for the treatment of anxiety and schizophrenia. Accordingly, in another of its aspects, the present invention provides pharmaceutical compositions useful to treat D4-related medical conditions, in which a compound of Formula II is present in an amount effective to antagonize D4 receptor stimulation, together with a pharmaceutically acceptable carrier. Compounds of Formula II are those compounds embraced by Formula I, but further include the compounds in which $R_2$ is phenyl or 3,4-dimethoxyphenyl. In another of its aspects, the invention provides a method for treating medical conditions for which a D4 antagonist is indicated, which comprising the step of administering to the patient an amount of a compound of Formula II effective to antagonize D4 receptor stimulation, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula II compound or a pharmaceutically acceptable salt, solvate or hydrate thereof, in an amount effective to antagonize D4 receptor stimulation.

The compounds of the present invention may be administered by any convenient route, for example by oral, parenteral, buccal, sublingual, nasal, rectal or transdermal administration and the pharmaceutical compositions formulated accordingly. Compounds of Formula I and II and their stereoisomers, solvates, hydrate, or pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of them examples will be roughly equivalent to, or slightly less than, those used currently for clozapine. Accordingly, each dosage unit for oral administration may contain from 1 to about 500 mgs, and will be administered in a frequency appropriate for initial and maintenance treatments.

For laboratory use as a ligand, the present compounds can be stored in packaged form for reconstitution and use. The present compounds can be used to distinguish dopamine receptors from other receptor types, for example glutamate and opioid receptors, within a population of receptors and in particular to distinguish between the D4 and D2 receptors. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting lesser radioactivity, i.e., lesser $^3$H-spiperone binding.

In another embodiment of the invention, the compound is provided in labelled form, such as radiolabelled form e.g. labelled by incorporation within its structure of $^3$H or $^{14}$C or by conjugation to $^{125}$I or $^{123}$I. Such radiolabelled forms can be used directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

EXAMPLE 1(a)

2-(4-Piperonyl-1-piperazinyl)-2,4,6-cycloheptatriene-1-one

A mixture of 2-methoxytropone (1.36 g, 10.0 mmol) (Pietra, F. Chem Review, 1973, 73:293) and 1-piperonylpiperazine (6.61 g, 30.0 mmol) in methanol (50.0 mL) was refluxed for 16 h. After cooling to room temperature, the solvent was removed in vacuo. The residue was subjected to column chromatography using ethyl acetate as the eluent. The title compound was obtained as a yellow oil (1.24 g, 38%). MS (FAB) 325 (M$^+$+1).

In a like manner, the following additional compound was prepared:
(b) 7-bromo-2-(4-piperonyl-1-piperazinyl)-2,4,6-cycloheptatriene-1-one, from 7-bromo-2-methoxytropone (Takeshita, H.; Mori, A. Synthesis, 1986, 578).

EXAMPLE 2(a)

2-(1-piperazinyl)-2,4,6-cycloheptatriene-1-one acetic acid salt

This compound was prepared from 2-methoxytropone and piperazine according to the procedure of Bagli, J. et al., J. Med. Chem. 1984, 27:875.

In a like manner, the following addition compound was prepared:
(b) 7-bromo-2-(1-piperazinyl)-2,4,6-cycloheptatriene-1-one acetic acid salt.

EXAMPLE 3(a)

2-[4-(3-Methoxybenzyl)-1-piperazinyl]-2,4,6-cycloheptatriene-1-one

A mixture of 2-(1-piperazinyl)-2,4,6-cycloheptatriene-1-one acetic acid salt (0.171 g, 0.680 mmol, example 2a), 3-methoxybenzyl chloride (0.118 g, 0.750 mmol) and potassium carbonate (0.276 g, 2.00 mmol) in acetonitrile (2.00 mL) was stirred at room temperature for 16 h. The solvent was removed in vacuo. The residue was triturated with dichloromethane and filtered. The filtrate was concentrated in vacuo to dryness and the residue was subjected to preparative thin layer chromatography using ethyl acetate-:methanol (9:1) as the eluent. The title compound was obtained as a yellow oil (0.095 g, 45%); MS (FAB) 311 (M$^+$+1).

In a like manner, the following additional compounds were prepared:

b) 2-(4-hexyl-1-piperazinyl)-2,4,6-cycloheptatriene-1-one, from 1-bromohexane; yellow oil (51%); MS (ES) 275 (M$^+$+1).

c) 2-[4-(4-cyanobenzyl)-1-piperazinyl]-2,4,6-cycloheptatriene-1-one, from 4-cyanobenzyl bromide; yellow solid (44%); m.p. 136–138° C.; MS (FAB) 306 (M$^+$+1).

d) 2-[4-benzyl-1-piperazinyl]-2,4,6-cycloheptatriene-1-one, from benzyl bromide.

e) 2-[4-(4-methylbenzyl)-1-piperazinyl]-2,4,6-cycloheptatriene-1-one, from α-bromo-p-xylene; MS (FAB) 295 (M$^+$+1).

f) 2-[4-(4-trifluoromethoxybenzyl)-1-piperazinyl]-2,4,6-cycloheptatriene-1-one, from 4-(trifluoromethoxy)benzyl bromide; MS (FAB) 365 (M$^+$+1).

g) 2-[4-(4-trifluoromethylbenzyl)-1-piperazinyl]-2,4,6-cycloheptatriene-1-one, from α'-bromo-α,α,α-trifluoroxylene; m.p. 111–113° C.; HRMS (FAB): MH$^+$ for $C_{19}H_{19}F_3N_3O$, Calc'd 349.1529, Found 349.1528.

h) 2-[4-(4-nitrobenzyl)-1-piperazinyl]-2,4,6-cycloheptatriene-1-one, from 4-nitrobenzyl bromide; m.p. 108–110° C.; HRMS (FAB): MH$^+$ for $C_{18}H_{19}N_3O_3$, Calc'd 326.1506, Found 326.1512.

i) 2-[4-(3-cyanobenzyl)-1-piperazinyl]-2,4,6-cycloheptatriene-1-one, from α-bromo-m-tolunitrile.

j) 2-[4-(3-trifluoromethylbenzyl)-1-piperazinyl]-2,4,6-cycloheptatriene-1-one, from α'-bromo-α,α,α-trifluoro-m-xylene; MS (FAB) 349 (M$^+$+1).

k) 2-[4-(4-bromobenzyl)-1-piperazinyl]-2,4,6-cycloheptatriene-1-one, from 4-bromobenzyl bromide; m.p. 122–124° C.; MS (FAB) 359 (M$^+$+1).

l) 2-(2-methyl-4-naphthyl-1-piperazinyl)-2,4,6-cycloheptatriene-1-one, from 2-(bromomethyl)-naphthalene; MS (FAB) 331 (M$^+$+1).

m) 2-[4-(3,5-difluorobenzyl)-1-piperazinyl]-2,4,6-cycloheptatriene-1-one, from α-bromo-3,5-difluorotoluene.

n) 2-[4-(2-cyanobenzyl)-1-piperazinyl]-2,4,6-cycloheptatriene-1-one, from α-bromo-o-tolunitrile.

o) 2-[4-(2-chlorobenzyl)-1-piperazinyl]-2,4,6-cycloheptatriene-1-one, from 2-chlorobenzyl bromide.

p) 2-[4-(2-nitrobenzyl)-1-piperazinyl]-2,4,6-cycloheptatriene-1-one, from 2-nitrobenzyl bromide.

q) 2-[4-(3-methylbenzyl)-1-piperazinyl]-2,4,6-cycloheptatriene-1-one, from α-bromo-m-xylene.

r) 2-{4-[1-(6,7-dimethoxycoumarin)methyl]-1-piperazinyl}-2,4,6-cycloheptatriene-1-one, from 4-(bromomethyl)-6,7-dimethyoxycoumarin.

s) 2-{4-[1-(7-methoxycoumarin)methyl]-1-piperazinyl}-2,4,6-cycloheptatriene-1-one, from 4-(bromomethyl)-7-methyoxycoumarin.

t) 2-[4-(2-phenylbenzyl)-1-piperazinyl]-2,4,6-cycloheptatriene-1-one, from 2-(bromomethyl)biphenyl.

u) 2-[4-(3-bromobenzyl)-1-piperazinyl]-2,4,6-cycloheptatriene-1-one, from 3-bromobenzyl bromide.

v) 2-{4-[3,5-bis(trifluoromethyl)benzyl]-1-piperazinyl}-2,4,6-cycloheptatriene-1-one, from 3,5-bis(trifluoromethyl) benzyl bromide.

w) 2-[4-(3-nitrobenzyl)-1-piperazinyl]-2,4,6-cycloheptatriene-1-one, from 3-nitrobenzyl bromide.

x) 2-[4-(4-chlorobenzyl)-1-piperazinyl]-2,4,6-cycloheptatriene-1-one, from 4-chlorobenzyl bromide; HRMS (FAB): MH$^+$ for $C_{18}H_{19}ClN_2O$, Calc'd 315.1264, Found 315.1270.

y) 2-[4-(3-chlorobenzyl)-1-piperazinyl]-2,4,6-cycloheptatriene-1-one, from 3-chlorobenzyl bromide; HRMS (FAB): MH$^+$ for $C_{18}H_{19}ClN_2O$, Calc'd 315.1264, Found 315.1258.

z) 7-bromo-2-[4-(4-chlorobenzyl)-1-piperazinyl]-2,4,6-cycloheptatriene-1-one, from 7-bromo-2-(1-piperazinyl)-2,4,6-cycloheptatriene-1-one of example 2b and 4-chlorobenzyl bromide.

EXAMPLE 4(a)

2-(4-Piperonyl-1-piperazinyl)-2,4,6-cycloheptatriene-1-one, maleic acid salt 2-(4-Piperonyl-1-piperazinyl)-2,4,6-cycloheptatriene-1-one (0.949 g, 2.92 mmol, example 1a) was dissolved in diethyl ether (15.0 mL) and a solution of maleic acid (0.373 g, 3.22 mmol) in methanol (0.50 mL) was added. The resulting mixture was stirred at room temperature for 16 h. Filtration of the mixture gave the maleic acid salt as a yellow solid (1.09 g, 85%); m.p. 142–144° C.; MS (ES) 325 (M$^+$—$C_4H_4O_4$).

In a like manner, the maleic acid salts of the following additional compounds were prepared:

b) 2-[4-(4-trifluoromethoxybenzyl)-1-piperazinyl]-2,4,6-cycloheptatriene-1-one (example 3f); m.p. 170–172° C.; HRMS (FAB): MH$^+$ for $C_{19}H_{19}F_3N_2O_2$ (free base), Calc'd 365.1523, Found 365.1477.

c) 2-(2-methyl-4-naphthyl-1-piperazinyl)-2,4,6-cycloheptatriene-1-one (example 3l); m.p. 170–172° C.

EXAMPLE 5

2-(4-Piperonyl-1-piperazinyl)7-thien2-yl-2,4,6-cycloheptatriene-1-one

To a solution of 2-bromothiophene (1.0 g, 6.1 mmol) in tetrahydrofuran (50 mL) at −78° C., was added n-butyl lithium (1.6 M in cyclohexane, 4.0 mL) and the resulting solution was stirred for 5 minutes. At this time, ZnCl$_2$ (0.5 M in THF, 20 mL) was added and the solution was warmed to room temperature over 2 hours. To the reaction mixture was then added palladium tetrakis(triphenylphosphine) (200 mg) and a solution of the acetic acid salt of 7-bromo-2-(4-piperonyl-1-piperazinyl)-2,4,6-cycloheptatriene-1-one (300 mg, 0.74 mmol, example 1b) in tetrahydrofuran (5 mL) and the resulting mixture was refluxed for 18 hours. The reaction was quenched with a saturated aqueous ammonium chloride solution and the product, extracted into methylene chloride (3×200 mL). The crude product was purified by silica gel chromatography to provide the title compound as a dark yellow oil (50 mg, 50%).

EXAMPLE 6

Receptor Binding Assay

D2 and D4 receptor-binding affinities of the compounds of examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at −80° C. until used in binding assay. When used in the assay, cells were thawed on ice for 20 min and then 10 ml of incubation buffer (50 mM Tris, 1 mM EDTA, 4 mM MgCl$_2$, 5 mM KCl, 1.5 mM CaCl$_2$, 120 mM NaCl, pH 7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation

GH$_4$C$_1$ (rat pituitary) cells stably transfected with the human D2 receptor (short isoform) were grown in HAM'S F10 media in NUNC cell factories for 5 days. 100 μM ZnSO$_4$ was added to the cells (the D2 promoter being zinc inducible). After 16 hours, fresh media was added to allow the cells to recover for 24 hours. The cells were harvested using versine and then centrifuged in a Sorval centrifuge for 10 minutes, at 5000 rpm (GS3 rotor). Pellets were quickly frozen in liquid nitrogen and stored at −80° C. until used in the binding assays. When used in the assay, cells were thawed on ice for 20 minutes. Each cell factory produced approximately 72 mg of protein. 10 ml of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 100 μl (50 μg protein) membrane homogenate to a solution of 300 μl incubation buffer and 100 μl (0.25 nM final conc.) $^3$H-spiperone (90 Ci/mmol Amersham diluted in borosilicate glass vial) in 96-well polypropylene plates (1 mL per well). The plates were vortexed and incubated at room temperature for 90 minutes. The binding reaction was stopped by filtering using a Packard Harvester. The samples were filtered under vacuum over glass fibre filter plates (Whatman GF/B) presoaked for 2 hours in 0.3% polyethylenimine (PEI) in 50 mM Tris buffer (pH 7.4). The filters were then washed 6 times with 7 ml ice cold 50 mM Tris buffer (pH 7.4). The filter plates were dried overnight and 35 μl of Microscint-O (Packard) was added. The plates were sealed and counted in the Packard Top Count (3 minutes per well).

Non-specific Binding Assay for D4

The incubation was started by the addition of 100 μl (50 μg protein) membrane homogenate to a solution of 200 μl incubation buffer, 100 μl $^3$H-spiperone (90 Ci/mmol Amersham diluted in borosilicate glass vial to 0.25 nM final conc.) and 100 μl (30 μM final conc.) of fresh dopamine (Research Biochemicals Inc., light protected and dissolved in incubation buffer) in 96-well polypropylene plates (1 mL per well).

The plates were vortexed and incubated at room temperature for 90 minutes at which time the binding reaction was stopped by filtering. The filters were washed and counted using the same procedure as in the total binding assay described above to give the non-specific binding value (NSB).

Non-specific Binding Assay for D2

This assay employed the same procedures as the non-specific binding assay for D4 with the exception that 2 μM (final conc.) of (−) sulpiride (Research Chemicals Inc.) was used in place of dopamine.

Displacement Binding Assay

The incubation was started by the addition, in 96-well polypropylene plates (1 mL per well), of 100 μl (50 μg protein) membrane homogenate to a solution of 200 μl incubation buffer, 100 μl (0.25 final conc.) $^3$H-spiperone (90 Ci/mmol, Amersham, diluted in borosilicate glass vial) and 100 μl of test compound that was prepared from 1 mM stock dissolved in DMSO and stored at −20° C. in polypropylene cryogenic storage vials until dilution in incubation buffer in 96-well polypropylene plates. The plates were vortexed and incubated at room temperature for 90 minutes at which time the binding reaction was stopped by filtering. The filters were washed and counted using the same procedure as in the total binding assay described above to give the displacement binding value (B$_D$).

Calculations

The test compounds were initially assayed at 1 and 0.1 μM and then at a range of concentrations chosen such that the middle dose would cause about 50% inhibition of $^3$H-spiperone binding. Specific binding in the absence of test compound (B$_0$) was the difference of total binding (B$_T$) minus non-specific binding (NSB) and similarly specific binding (in the presence of test compound) (B) was the difference of displacement binding (B$_D$) minus non-specific binding (NSB). IC$_{50}$ was determined from an inhibition response curve, logit-log plot of %B/B$_0$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and K$_D$ is the dissociation constant of $^3$H-spiperone determined independently under the same binding conditions.

Assay results are reported in the following Table, and show clearly the advantage in terms of D4 selectivity and or binding affinity of compounds of the invention over clozapine.

D4 AFFINITY AND SELECTIVITY

| COMPOUND | STRUCTURE | Ki (nm) | D2/D4 |
| --- | --- | --- | --- |
| clozapine | 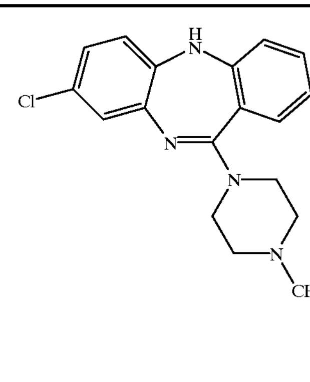 | 23 | 10 |

-continued

| COMPOUND | STRUCTURE | Ki (nm) | D2/D4 |
|---|---|---|---|
| 2-(4-piperonyl-1-piperazinyl)-2,4,6-cycloheptatriene-1-one | 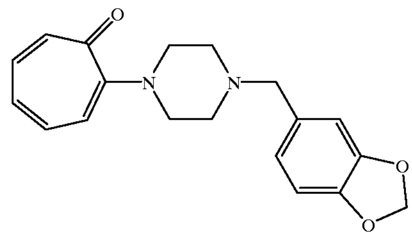 | 7.15 | 154 |
| 2-(4-hexyl-1-piperazinyl)-2,4,6-cycloheptatriene-1-one | 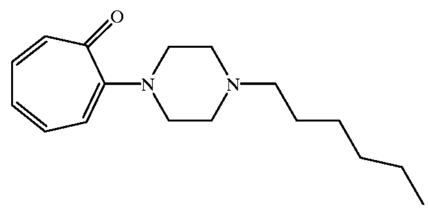 | 33.3 | 23 |
| 2-[4-(4-cyanobenzyl)-1-piperazinyl]-2,4,6-cycloheptatriene-1-one | 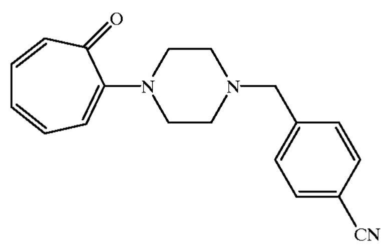 | 29.5 | 169 |
| 2-[4-(3-methoxybenzyl)-1-piperazinyl]-2,4,6-cycloheptatriene-1-one | 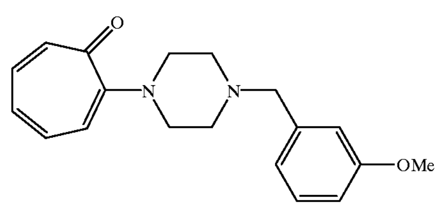 | 19.2 | 137 |
| 2-[4-(4-bromobenzyl)-1-piperazinyl]-2,4,6-cycloheptatriene-1-one | 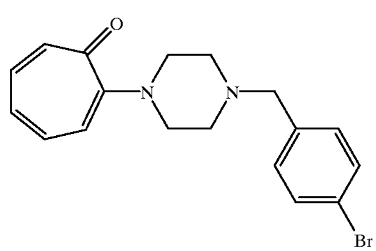 | 0.82 | 935 |

D4 AFFINITY AND SELECTIVITY

| COMPOUND | STRUCTURE | Ki (nm) | D2/D4 |
|---|---|---|---|
| 2-[4-(4-trifluoromethoxybenzyl)-1-piperazinyl]-2,4,6-cyoloheptatriene-1-one | 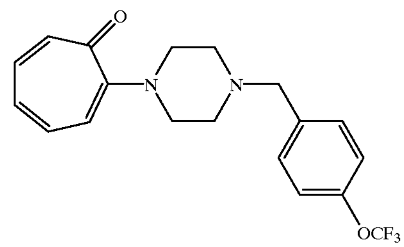 | 2.18 | 367 |
| 2-[4-(4-trifluoromethylbenzyl)-1-piperazinyl]-2,4,6-cycloheptatriene-1-one | 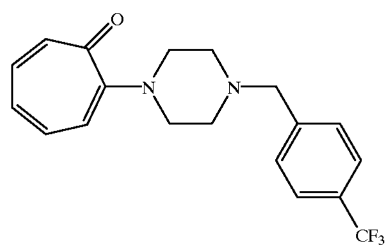 | 4.22 | 598 |
| 2-[4-(4-nitrobenzyl)-1-piperazinyl]-2,4,6-cycioheptatriene-1-one | 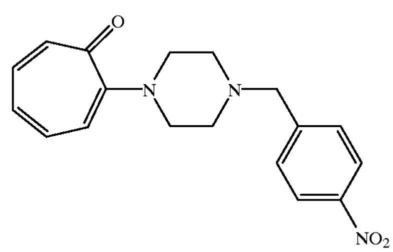 | 6.67 | 1014 |
| 2-[4-(3-trifluoromethylbenzyl)-1-piperazinyl]-2,4,6-cycloheptatriene-1-one | 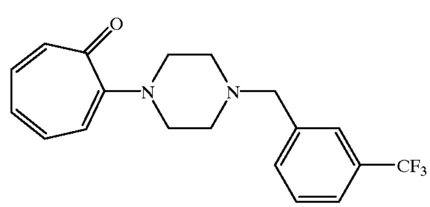 | 21.5 | 28 |
| 2-(4-naphthyl-2-benzyl-1-piperazinyl)-2,4,6-cycloheptatriene-1-one | 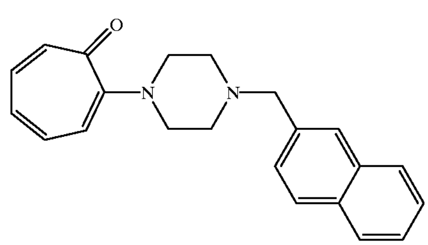 | 2.24 | 321 |

-continued

D4 AFFINITY AND SELECTIVITY

| COMPOUND | STRUCTURE | Ki (nm) | D2/D4 |
|---|---|---|---|
| 2-[4-(3-chlorobenzyl)-1-piperazinyl]-2,4,6-cycloheptatriene-1-one | | 16.4 | 47 |
| 2-[4-(3-bromobenzyl)-1-piperazinyl]-2,4,6-cycloheptatriene-1-one | 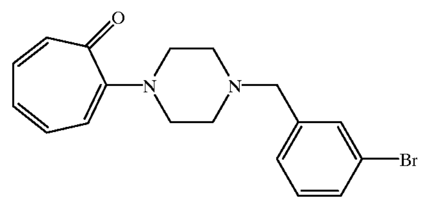 | 9.58 | 53 |
| 2-[4-(4-methylbenzyl)-1-piperazinyl]-2,4,6-cycloheptatriene-1-one | 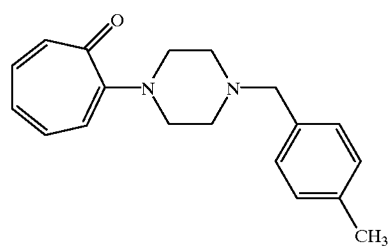 | 1.46 | 443 |
| 2-[4-(3-chlorobenzyl)-1-piperazinyl]-2,4,6-cycloheptatriene-1-one | | 1.41 | 805 |
| 7-bromo-2-(4-piperonyl-1-piperazinyl)-2,4,6-cycloheptatriene-1-one | 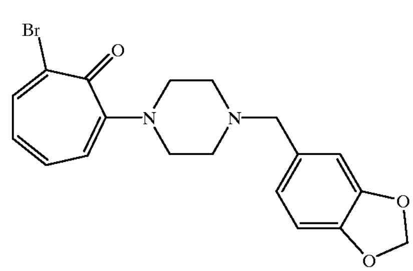 | 0.226 | 104 |

D4 AFFINITY AND SELECTIVITY

| COMPOUND | STRUCTURE | Ki (nm) | D2/D4 |
|---|---|---|---|
| 2-(4-piperonyl-1-piperazinyl)-7-thien-2-yl-2,4,6-cycloheptatriene-1-one | 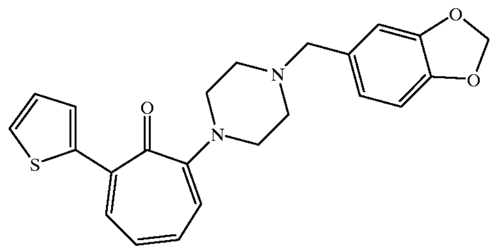 | 11.9 | 34 |

EXAMPLE 7

Functional Assay

The D4 receptor responds to dopamine and other agonists by reducing adenyl cyclase mediated production of cyclic AMP. Particular test compounds were assayed for their ability to reverse dopamine inhibition of adenyl cyclase by the following procedure. Forskolin was used to elevate the basal adenyl cyclase activity.

CHO Pro 5 cells stably expressing human D4.2 receptors were plated in 6 well plates in DMEM (Dulbecco's Modified Eagle Medium)/F12(Nutrient Mixture F12 (Ham)) media with 10% FCS (fetal calf serum) and G418 (Geneticen Disulfate), and incubated at 37° C. in a $CO_2$ incubator. The cells were allowed to grow to about 70% confluence before use in the assay.

Antagonist Assay

The culture media of each well was removed, and the wells were washed once with serum free media (SFM) (DMEM/F12) media. Then 2 mL of fresh SFM+IBMX media (SFM with 0.5 mM IBMX, 3-isobutyl-1-methylxanthine, 0.1% ascorbic acid and 10 $\mu$M pargyline) was added to each well and then incubated at 37° C. for 10 minutes in a $CO_2$ incubator. Following incubation, SFM+IBMX media was removed and fresh SFM+IBMX media was added to wells separately with one of a) forskolin (10 $\mu$M final conc.); b) dopamine and forskolin (both 10 $\mu$M final conc.); and c) test compound ($10^{-4}$ to $10^{-6}$ M), and dopamine and forskolin (both 10 $\mu$M final conc.). Basal adenyl cyclase activity was determined from wells with only SFM+IBMX media added.

The cells were then incubated at 37° C. for 30 minutes in a $CO_2$ incubator. Following incubation the media was removed from each well and then washed once with 1 mL of PBS (phosphate buffered saline). Each well was then treated with 1 mL cold 95% ethanol:5 mM EDTA (2:1) at 4° C. for 1 hr. The cells from each well were then scraped and transferred into individual Eppendorf tubes. The tubes were centrifuged for 5 min at 4° C., and the supernatants were transferred to new Eppendorf tubes. The pellets were discarded and the supernatants stored at 4° C. until assayed for cAMP concentration. cAMP content measured in fmoles/well for each extract was determined by EIA (enzyme-immunoassay) using Amersham Biotrak cAMP EIA kit (Amersham RPN 225).

Total inhibition ($I_0$) of forskolin-stimulated adenyl cyclase activity by dopamine was determined as the difference in concentration of cAMP in the forskolin-treated cells ($C_f$) and dopamine-forskolin treated cells ($C_d$).

$$I_0 = C_f - C_d$$

Net inhibition (I) of forskolin-stimulated adenyl cyclase activity by dopamine in the presence of an antagonist was determined as the difference in concentration of cAMP in the forskolin-treated cells ($C_f$) and test compound, dopamine and forskolin treated cells (C).

$$I = C_f - C$$

The ability of the test compounds to reverse the dopamine inhibition (% reversal, % R) was determined by the formula:

$$\% R = (1 - I/I_0) \times 100$$

| | % REVERSAL OF DOPAMINE EFFECT | |
|---|---|---|
| COMPOUND | 1 $\mu$M | 10 $\mu$M |
| clozapine | 6 | 58 |
| 2-(4-piperonyl-1-piperazinyl)-2,4,6-cycloheptatriene-1-one | 32 | 65 |
| 2-(4-hexyl-1-piperazinyl)-2,4,6-cycloheptatriene-1-one | 45 | 50 |

Agonist Assay

To D4.2 stably expressing CHO cells prepared as previously described were added test compound and forskolin (10 $\mu$M final concentration). The cells were incubated, extracted and measured for cAMP concentration as above. Agonist activity of a test compound would result in a decrease in cAMP concentration compared to cells treated with forskolin ($C_f$) only. No decrease was observed, therefore the test compounds exhibited no dopamine agonist activity. It is predicted based on structural and biological functional similarities that the remaining compounds of the invention would also exhibit dopamine antagonist activity.

We claim:

1. A compound of the following formula:

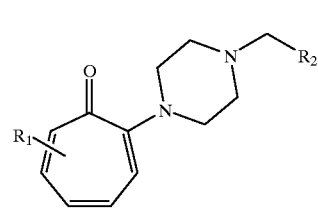

a stereoisomer, or pharmaceutically acceptable salt thereof, wherein:

R₁ is thienyl, at the 7 position of the 7-membered ring;

R₂ is 4-methylphenyl; 4-trifluoromethoxyphenyl; 4-trifluoromethylphenyl; 4-nitrophenyl; 3-cyanophenyl; 3-trifluoromethylphenyl; 4-bromophenyl; 3,5-difluorophenyl; 2-cyanophenyl; 2-chlorophenyl; 2-nitrophenyl; 3-methylphenyl; 2-phenylphenyl; 3-bromophenyl; 3-,5-bis(trifluoromethyl)phenyl; 3-nitrophenyl; 4-cyanophenyl; 3-methoxyphenyl; 2-naphthyl; 3-chlorophenyl, 4-chlorophenyl or 1,2-methylenedioxyphenyl;

R₃ and R₄ are selected independently from H, C₁₋₄alkyl, C₁₋₄alkoxy; or 1,2-methylenedioxy phenyl.

2. A pharmaceutical composition comprising a therapeutically effective amount of the compound of claim 1 and a pharmaceutically acceptable carrier.

3. A method of treating a patient for schizophrenia comprising administering to the patient a therapeutically effective amount of the compound of claim 1.

4. A method of making a compound according to claim 1, comprising the steps of coupling a reagent of the following formula, wherein R1 has the same meaning as in claim 1:

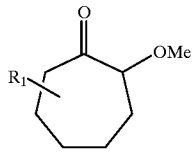

with a reagent of the following formula, wherein R2 has the same meaning as in claim 1:

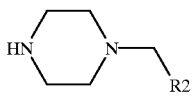

in refluxing methanol to produce the compound of claim 1.

5. A compound of the following formula:

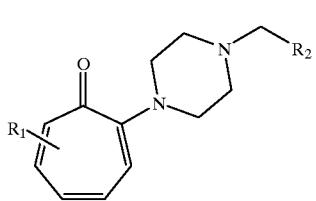

I a stereoisomer, or pharmaceutically acceptable salt thereof, wherein:

R₁ is H;

R₂ is 1-(6,7-dimethoxycourmarinyl) or 1-(7-methoxycoumarinyl); and

R₃ and R₄ are selected independently from H, C₁₋₄alkyl, C₁₋₄alkoxy or 1,2-methylenedioxyphenyl.

6. A pharmaceutical composition comprising a therapeutically effective amount of the compound of claim 5 and a pharmaceutically acceptable carrier.

7. A method of treating a patient for schizophrenia comprising administering to the patient a therapeutically effective amount of a compound according to claim 5.

8. A method of making a compound according to claim 5, comprising the steps of coupling a reagent of the following formula, wherein R1 has the same meaning as in claim 5:

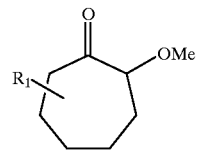

with a reagent of the following formula, wherein R2 has the same meaning as in claim 5:

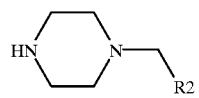

in refluxing methanol to produce the compound of claim 5.

9. A compound, or its pharmaceutically acceptable salt, wherein the compound is 2-(4-piperonyl-1-piperazinyl)-2,4,6-cycloheptatriene-1-one.

10. A compound, or its pharmaceutically acceptable salt, wherein the compound is 2-[4-(4-cyanobenzyl)-1-piperazinyl]-2,4,6-cycloheptatriene-1-one.

11. A compound, or its pharmaceutically acceptable salt, wherein the compound is 2-[4-(4-trifluoromethoxybenzyl)-1-piperazinyl]-2,4,6-cycloheptatriene-1-one.

12. A compound, or its pharmaceutically acceptable salt, wherein the compound is 2-[4-(4-nitrobenzyl)-1-piperazinyl]-2,4,6-cycloheptatriene-1-one.

13. A compound, or its pharmaceutically acceptable salt, wherein the compound is 2-[4-(3-cyanobenzyl)-1-piperazinyl]-2,4,6-cycloheptatriene-1-one.

14. A compound, or its pharmaceutically acceptable salt, wherein the compound is 2-[4-(2-naphthalenylmethyl)-1-piperazinyl]-2,4,6-cycloheptatriene-1-one.

15. A compound, or its pharmaceutically acceptable salt, wherein the compound is 2-[4-(2-phenylbenzyl)-1-piperazinyl]-2,4,6-cycloheptatriene-1-one.

16. A compound, or its pharmaceutically acceptable salt, wherein the compound is 2-[4-(3-nitrobenzyl)-1-piperazinyl]-2,4,6-cycloheptatriene-1-one.

17. A compound, or its pharmaceutically acceptable salt, wherein the compound is 7-bromo-2-[4-(4-chlorobenzyl)-1-piperazinyl]-2,4,6-cycloheptatriene-1-one.

18. A compound, or its pharmaceutically acceptable salt, wherein the compound is 7-bromo-2-(4-piperonyl-1-piperazinyl)-2,4,6-cycloheptatriene-1-one.

19. A compound, or its pharmaceutically acceptable salt, wherein the compound is 2-(4-piperonyl-1-piperazinyl)-7-thien-2-yl-2,4,6-cycloheptatriene-1-one.

20. A compound, or its pharmaceutically acceptable salt, wherein the compound is 2-{4-[1-(6,7-dimethoxycoumarinyl)methyl-1-piperazinyl]-2,4,6-cycloheptatriene-1-one.

21. A compound, or its pharmaceutically acceptable salt, wherein the compound is 2-{4-[1-(7-methoxycoumarinyl)methyl-1-piperazinyl]-2,4,6-cycloheptatriene-1-one.

22. A method of treating a patient for schizophrenia comprising administering to the patient a therapeutically effective amount of a compound according to one of claims 9–21.

23. A pharmaceutical composition comprising a therapeutically effective amount of one of the compounds of claims 9–21 and a pharmaceutically acceptable carrier.

* * * * *